United States Patent [19]

Chopdekar

[11] 4,036,889
[45] July 19, 1977

[54] PROCESS FOR PREPARING TRIARYLPHOSPHINES
[75] Inventor: Vilas M. Chopdekar, Parlin, N.J.
[73] Assignee: M & T Chemicals Inc., Greenwich, Conn.
[21] Appl. No.: 608,051
[22] Filed: Aug. 27, 1975
[51] Int. Cl.$^2$ .............................................. C07F 9/02
[52] U.S. Cl. ........................ 260/606.5 P; 252/426; 252/429 R
[58] Field of Search .................................. 260/606.5 P
[56] References Cited
U.S. PATENT DOCUMENTS 3,723,536  3/1973  Stuebinger ................... 260/606.5 P
3,751,481  8/1973  Weinberg ..................... 260/606.5 P
3,751,482  8/1973  Weinberg ..................... 260/606.5 P

OTHER PUBLICATIONS

Horner et al., Chem. Bericht 92, (1959), pp. 2088-2094.

Primary Examiner—Arthur P. Demers
Attorney, Agent, or Firm—Robert P. Auber; Kenneth G. Wheeless; Robert Spector

[57] ABSTRACT

Triarylphosphines are prepared in high yield and purity by the reaction between sodium, a monohalogenated aromatic hydrocarbon and a phosphorus trihalide using a triphenylphosphine dihalide as the catalyst for said reaction.

4 Claims, No Drawings

PROCESS FOR PREPARING TRIARYLPHOSPHINES

BACKGROUND

This invention relates to the preparation of triarylphosphines. This invention further relates to a novel catalyst for preparing triarylphosphines by the reaction between sodium, an aryl halide and a phosphorous trihalide.

The preparation of triphenylphosphine from sodium, phosphorous trichloride and chlorobenzene was reported in the patent literature as early as 1930 (German Pat. No. 508,667). This patent teaches that certain catalysts can be added for the purpose of reducing the length of the induction period, which can be as long as one hour. Following the induction period the reaction may begin violently and is often accompanied by a large increase in the temperature of the reaction mixture. The heat generated may be sufficient to decompose a portion of the reactants, thereby decreasing product yield and purity.

U.S. Pat. No. 3,723,536 teaches that aryl halides or a small amount of a previously prepared triarylphosphine can be employed as a catalyst for the preparation of triarylphosphines, however, it has been found that these catalysts may have the same disadvantages as catalysts disclosed in the aforementioned German patent.

It is therefore an objective of this invention to provide a catalyst for the reaction of sodium, a monohalogenated aromatic hydrocarbon and a phophorus trihalide which will significantly reduce the induction period and the exothermic nature of this reaction while simultaneously improving product yield and purity. It has now been found that this objective can be achieved using a triarylphosphine dihalide as the catalyst for the reaction.

SUMMARY OF THE INVENTION

The present invention provides an improved method for preparing triarylphosphines of the general formula $Ar_3P$, wherein Ar represents an aromatic hydrocarbon radical selected from the group consisting of phenyl, naphthyl and anthracenyl radicals, by reacting a dispersed form of sodium, a monohalogenated aromatic hydrocarbon of the formula ArX, wherein X represents chlorine, bromine or iodine, and a phosphorus trihalide of the formula PX, at a temperature of between ambient and 80°C. in the presence of a liquid hydrocarbon dliuent and an effective amount of a catalyst. The improvement resides in selecting as the catalyst a triarylphosphine dihalide of the formula $Ar_3PX_2$.

DETAILED DESCRIPTION OF THE INVENTION

The present method for preparing triarylphosphines employs what has become known as a Wurtz-Fittig type of reaction between sodium, the halogen atoms of a phosphorus trihalide and the halogen atom of a monohalo substituted aromatic hydrocarbon. These reactions are often difficult to initiate, however once initiated may proceed violently and may be highly exothermic, particularly if large volumes of the halogenated hydrocarbon and phosphorus trihalide are present in the reaction mixture. These reagents are conventionally added gradually to the dispersed sodium over an extended period of time. Surprisingly it has been found that if a catalytic amount of a triarylphosphine dihalide, such as triphenylphospine dichloride, is present in the sodium dispersion the reaction begins within a few minutes following addition of a small portion of the aryl halide-phosphorus trihalide mixture, as evidenced by an increase in the temperature of the reaction mixture to between 60° and 70°C.

The sodium dispersion is conveniently prepared by heating a mixture of metallic sodium and a liquid aromatic hydrocarbon such as toluene or xylene to a temperature at least equal to the melting point of sodium (97.5°C.) with rapid stirring to ensure a uniformly small particle size for the sodium. The mixture is then cooled to solidify the dispersed sodium droplets. One of the present catalysts is added to this sodium dispersion in an amount equivalent to between 0.001 and 10%, based on the total weight of the three reagents. Following addition of the catalyst, the reaction is initiated by adding a small portion, usually between 1 and 5%, of the phosphorus trihalide monohaloaryl hydrocarbon mixture to the sodium dispersion. The mixture preferably contains the phosphorus trihalide and the hydrocarbon in approximately stoichiometric quantities, based on the molar amount of sodium present in the dispersion. It may be desirable to employ a slight excess over the stoichiometric amount of both components of this mixture. In an alternative procedure, the catalyst is present in this mixture rather than being added to the sodium dispersion as previously disclosed.

It may be necessary to heat the sodium dispersion to a temperature of between 40° and 80°C. to initiate the reaction. Once the reaction has begun, as evidenced by an abrupt increase in temperature, the remainder of the phosphorus trihalide-halogenated aryl hydrocarbon mixture is added gradually. The temperature of the reaction mixture is preferably maintained at between ambient and 80°C. during the addition of the aforementioned reagent mixture. The reaction mixture temperature can be controlled by cooling the reaction vessel or by varying the rate at which the reagent mixture is added. The time required for the addition is usually between 1 and 4 hours. This may vary somewhat depending upon the size of the reaction vessel, the volume of the reaction medium and the efficiency with which heat can be transferred out of the reaction mixture.

The monohalogenated aromatic hydrocarbon employed as one of the reagents in the present method exhibits the general formula ArX wherein Ar represents a phenyl, naphthyl or anthracenyl radical and X is chlorine, bromine or iodine. The Ar radical may contain inert substituents, for example alkoxy and alkyl radicals. Preferably Ar is a phenyl radical and X is chlorine. The monohalogenated aromatic hydrocarbon is added to the sodium dispersion concurrently with a phosphorus trihalide, $PX_3$. The halogen portion, represented by X, is usually identical to that present on the monohalogenated aromatic hydrocarbon, and is preferably chlorine. Preferably the same halogen is also present on the catalyst, a triarylphosphine dihalide. Thus, in a preferred embodiment of the method, chlorobenzene and phosphorus trichloride are reacted with a dispersed form of sodium in the presence of triphenylphosphine dichloride as the catalyst.

The concentration of catalyst is between 0.001 and 10% based on the combined weight of all reagents. It will be apparent to those skilled in the art that the lower concentrations would be employed as the total weight of reactants is increased.

The halogenated aromatic hydrocarbon and phosphorus trihalide can be supplied to the reaction vessel from separate sources or can be combined before being added to the reaction vessel. The latter alternative is preferred, since it ensures that the two reagents will be added in the proper stoichiometric ratio of three moles of halogenated aromatic hydrocarbon for each mole of phosphorus trihalide.

The triarylphosphines prepared in accordance with the present method are solid materials which are soluble in the reaction mixture. The byproduct, a sodium halide, is therefore readily isolated from the reaction mixture by filtration or decantation. The sodium halide is washed with a suitable organic solvent such as toluene to recover any triarylphosphine which may be adhering to it. If any unreacted sodium is present, it is conveniently disposed of by adding a stoichiometric amount of the same triarylphosphine dihalide previously employed as the catalyst for preparing the triarylphoshine. This method has the additional advantage of not introducing additional impurities, since sodium reacts with the triarylphosphine dihalide to yield the corresponding triarylphoshine.

In addition to reducing the time required to initiate the reaction between sodium, the halogenated aromatic hydrocarbon and the phosphorus trihalide, the present catalysts increase product yield and purity without using excess sodium as taught in the prior art. An additional advantage of the present catalysts is that they make it possible to stop the reaction before all of the reagents have been added. The reaction can be reinitiated at some later time simply by adding additional catalyst. This has not been feasible heretofore using prior art catalysts. This feature is particularly desirable when for one reason or another, it becomes necessary to interrupt for a substantial period of time the addition of phosphorus trihalide and halogenated aromatic hydrocarbon to the reaction vessel. The following examples demonstrate preferred embodiments of the present method and compare this method with products obtained using prior art catalysts.

EXAMPLE 1

A reaction vessel which had been previously flushed with dry nitrogen was charged with 125 cc. of toluene and 20 g. (0.834 g. atom) of sodium metal in the form of small balls. The mixture was heated to 105°C. with rapid stirring to melt and disperse the sodium. Heating of the reaction vessel was discontinued and the temperature of the contents gradually decreased to 55°C., at which time 1 g. of triphenylphosphine dichloride was added, followed by a 3 cc. portion of a mixture containing 48.9 g. (0.432 mole) of chlorobenzene and 19.8 g. (0.144 mole) of phosphorus trichloride. Initiation of the reaction occurred in three minutes, as evidenced by a sudden increase in the temperature of the reaction mixture from 55° to 66°C. The reaction vessel was then cooled using dry ice (solid carbon dioxide) and the remaining portion of the chlorobenzene phosphorus trichloride mixture added at a uniform rate over a period of 92 minutes. Throughout this interval the temperature of the reaction mixture remained between 45° and 60°C. Following completion of the addition the reaction mixture was heated to 60°C. for two hours, at which time a 50 cc. portion of toluene was added. The resultant mixture was then stirred and allowed to cool for 10 minutes. The solid material, sodium chloride, in the reaction vessel was removed by filtration. The sodium chloride was then washed using two 35 cc. portions of toluene. A small portion of methanol was added to the sodium chloride to decompose any unreacted sodium metal. No evolution of hydrogen was observed, indicating that no unreacted sodium was present.

The liquid phase of the reaction mixture together with the two aforementioned portions of toluene were evaporated under reduced pressure. The weight of the recovered solid after being dried at 40°C. under reduced pressure was 36.4 g. (equivalent to a yield of 93.5%, when corrected to reflect the amount of catalyst employed). Upon analysis the solid was found to contain 98.7% by weight of triphenylphosphine, 1.2% of triphenylphosphine oxide and 0.1% of biphenyl. When the foregoing procedure was repeated using half the amount of catalyst (0.5 g.), the reaction initiated in 4 minutes. In this instance no excess of sodium was used and none was found following completion of the reaction. The product was obtained in 96.2% yield and, upon analysis, was found to contain 99.1% by weight of triphenylphosphine, 0.2% of biphenyl, 0.2% of triphenylphosphine oxide and 0.5% of unidentified byproducts.

For purposes of comparison, the foregoing procedure was repeated using 1) a stoichiometric amount of sodium and 2) triphenylphosphine as the catalyst. This catalyst is disclosed in Example 1 of U.S. Pat. No. 3,723,536, which is hereby incorporated by reference. The amounts of reagents employed were five times those disclosed in the foregoing procedure. No initiation was observed during a thirty minute period following addition of a small portion of the chlorobenzene-phosphorus trichloride mixture (about 5% of total mixture). During this period the reaction mixture was heated to 50°C. An additional amount of this mixture, equal to approximately 20% of the total was then added. The contents of the reaction vessel were stirred and heated to 50°C. for about 30 minutes, at which time a violent, exothermic reaction occurred. The heat generated was sufficient to force a portion of the reaction mixture through the reflux condenser which was attached to the reaction vessel. The hot mixture ignited upon coming in contact with atmospheric moisture.

EXAMPLE 2

This example demonstrates that prior art catalysts are less effective in reducing the induction period than the present catalysts.

Triphenylphosphine was prepared using the same procedure as described in the first section of the preceding example with the exception that 1.1 g. of triphenylphosphine was added to the mixture of toluene (125 cc.) and sodium metal (20 g.) prior to the time this mixture was heated to form the dispersion. The stoichiometric amount of sodium was employed. A 3 cc. portion of the chlorobenzene-phosphorus trichloride mixture was added when the temperature of the dispersion had cooled to 60°C. The resultant mixture was stirred for 14 minutes, at which time initiation of the reaction occurred, as evidenced by an abrupt increase in temperature. The remaining chlorobenzene-phosphorus trichloride mixture was added during a two hour period while the reaction vessel was cooled to maintain the temperature of the contents at between 50 and 60°C. The mixture was heated at 55°C. for an additional hour, and the triphenylphosphine isolated as described in the preceding example. The product was obtained in 91.2% yield and contained some unreacted sodium, which was omitted from the yield calculation. Analysis of the solid material revealed the following constituents:

triphenylphosphine — 99.3%
triphenylphosphine oxide — 0.7%

The yields and analyses of products obtained using the procedures described in the foregoing examples are summarized in the following table.

| Catalyst | (%) | Excess Sodium Added | Excess Sodium Recovered | Initiation Period (min.) | % $(\phi)_3$P in Crude Product | % Yield (Corrected for Catalyst) |
|---|---|---|---|---|---|---|
| $\phi PCl_2$ | (1.1) | yes (3.5%) | no | 3 | 98.7 | 93.5 |
|  | (0.55) | no | no | 4 | 99.1 | 96.2 |
| $\phi_3$P | (0.2) | no | —* | 60 | —* | —* |
| $\phi_3$P | (1.2) | no | yes | 14 | 99.3 | 91.2 |

*Violent, exothermic reaction occurred, reaction mixture forced out of vessel and ignited spontaneously.

I claim:

1. In an improved method for preparing triarylphosphines of the general formula Ar₃P, wherein Ar represents phenyl, naphthyl or anthracenyl, by dispersing molten sodium in a liquid hydrocarbon dilent, combining the resultant dispersion with a monohalogenated aromatic hydrocarbon of the formula ArX, wherein X is chlorine, bromine or iodine, a phosphorus trihalide PX₃, an effective amount of a catalyst, and reacting the resultant mixture at a temperature between ambient and 80°C., the improvement which resides in employing as said catalyst a triarylphosphine dihalide of the formula Ar₃PX₂.

2. An improved method for preparing triarylphosphines according to claim 1 wherein Ar is phenyl and X is chlorine.

3. An improved method for preparing triarylphosphines according to claim 1 wherein the concentration of catalyst is between 0.001 and 10%, based on the combined weight of sodium, monohalogenated aromatic hydrocarbon and phosphorus trihalide.

4. An improved method for preparing triarylphosphines according to claim 1 wherein the monohalogenated aromatic hydrocarbon, catalyst and phosphorus trihalide are gradually added to finely divided sodium which is dispersed in the liquid hydrocarbon diluent while maintaining the temperature of the reaction mixture at between ambient and 70°C.

* * * * *